United States Patent
Raa et al.

(10) Patent No.: US 10,485,779 B2
(45) Date of Patent: Nov. 26, 2019

(54) OIL COMPOSITION, FORMULATIONS COMPRISING THE OIL COMPOSITION, AND THE USE THEREOF TO REDUCE ACCUMULATION OF VISCERAL FAT, IMPROVE GLUCOSE TOLERANCE, AND PREVENT OR TREAT OBESITY RELATED DISEASES AND DISORDERS

(71) Applicant: Calanus AS, Tromso (NO)

(72) Inventors: Jan Raa, Oslo (NO); Gunnar Rorstad, Tromso (NO); Kurt Steinar Tande, Kvaloysletta (NO)

(73) Assignee: Calanus AS, Tromsø (NO)

( * ) Notice: Subject to any disclaimer, the term of this patent is extended or adjusted under 35 U.S.C. 154(b) by 667 days.

(21) Appl. No.: 14/141,492

(22) Filed: Dec. 27, 2013

(65) Prior Publication Data

US 2014/0105999 A1 Apr. 17, 2014

Related U.S. Application Data (62) Division of application No. 13/377,572, filed as application No. PCT/NO2010/000223 on Jun. 11, 2010, now abandoned.

(30) Foreign Application Priority Data

Jun. 12, 2009 (NO) .................................. 20092282

(51) Int. Cl.
*A61K 31/201* (2006.01)
*A61K 35/64* (2015.01)
(Continued)

(52) U.S. Cl.
CPC ............ *A61K 31/201* (2013.01); *A23D 9/013* (2013.01); *A23K 20/158* (2016.05);
(Continued)

(58) Field of Classification Search
CPC .. A61K 31/201; A61K 31/122; A61K 31/202; A61K 31/231; A61K 31/232;
(Continued)

(56) References Cited

U.S. PATENT DOCUMENTS 8,535,708 B2 9/2013 Wedekind et al.
2002/0025983 A1* 2/2002 Horrobin ...................... 514/560
(Continued)

FOREIGN PATENT DOCUMENTS

| JP | 2002-527604 | 8/2002 |
|---|---|---|
| JP | 2004-292421 | 10/2004 |

(Continued)

OTHER PUBLICATIONS

Waxes: retrieved from internet: http://lipidlibrary.aocs.org/Primer/content.cfm?ItemNumber=39369. Retrieved on Sep. 13, 2016.*
(Continued)

*Primary Examiner* — Hong Yu
(74) *Attorney, Agent, or Firm* — Christian D. Abel (57) ABSTRACT

This invention relates to an oil composition, preferably obtained from a copepod, and the use thereof to reduce accumulation of visceral fat and counteract impairment of heart function caused by obesity inducing Western diets. The oil composition of the present invention can thus be used to reduce abdominal obesity and improve glucose tolerance and thus to reduce the risk of obesity related diseases such as but not limited to type 2 diabetes or cardiovascular disease, or to prevent or treat such diseases.

11 Claims, 3 Drawing Sheets

(51) Int. Cl.

| | |
|---|---|
| *A23D 9/013* | (2006.01) |
| *A61K 31/122* | (2006.01) |
| *A61K 31/202* | (2006.01) |
| *A61K 31/231* | (2006.01) |
| *A61K 31/232* | (2006.01) |
| *A61K 35/612* | (2015.01) |
| *A61K 35/63* | (2015.01) |
| *A23K 20/158* | (2016.01) |
| *A23L 33/00* | (2016.01) |
| *A23L 33/115* | (2016.01) |
| *A23L 33/12* | (2016.01) |

(52) U.S. Cl.
CPC ............ *A23L 33/115* (2016.08); *A23L 33/12* (2016.08); *A23L 33/30* (2016.08); *A61K 31/122* (2013.01); *A61K 31/202* (2013.01); *A61K 31/231* (2013.01); *A61K 31/232* (2013.01); *A61K 35/612* (2013.01); *A61K 35/63* (2015.01); *A61K 35/64* (2013.01); *A23V 2002/00* (2013.01)

(58) Field of Classification Search
CPC ...... A61K 35/64; A61K 35/612; A61K 35/63; A23D 9/013; A23K 20/158; A23L 33/30; A23L 33/115; A23L 33/12; A23V 2002/00

See application file for complete search history.

(56) References Cited

U.S. PATENT DOCUMENTS

| | | | |
|---|---|---|---|
| 2006/0088574 A1 | 4/2006 | Manning et al. | |
| 2008/0274175 A1 | 11/2008 | Schramm et al. | |
| 2008/0274203 A1* | 11/2008 | Bruheim et al. | ............ 424/522 |

FOREIGN PATENT DOCUMENTS

| | | | |
|---|---|---|---|
| RU | 2264441 | 7/2001 | |
| RU | 2354136 | 5/2009 | |
| WO | 98/56883 | 12/1998 | |
| WO | 2004/028469 | 4/2004 | |
| WO | 2005/060954 | 7/2005 | |
| WO | WO 2008/132552 A2 * | 11/2008 | ............ C07C 33/02 |

OTHER PUBLICATIONS

A Oxley, et al., "Digestibility of Calanus finmarchicus wax esters in Atlantic Salmon (*Salmo salar*) freshwater presmolts ans seawater postsmolts maintained at constantwater temperature", Aquaculture Nutrition, (Oct. 6, 2008 publsihed online) 11,pp. 459-469.

Office action from Japan Patent Office dated Jun. 3, 2014 (and translation thereof), submitted, inter alia, as statement of relevance for non-English citations.

English translation of office action dated Jan. 9, 2014 from Russian Patent Office.

Catherine L. Scott et al: "Species differences, origins and functions of fatty alcohol and fatty acids in the wax esters and phospholipids of Calanus hyperboreus, C. glacialis and C. finmarchicus from Arctic waters", Marine Ecology Progress Series, 2002, vol. 235, p. 129-130.

Office action dated Feb. 20, 2014 from Russian Patent Office, with English translation.

Official Action from JApanese Patent Office dated Apr. 4, 2017, together with English Translation. Cited, inter alia, as a Statement of Relevance for non-English references cited therein.

R.E. Olsen, et.al. "Atlantic Salmon, *Salmo salar*, utilizes was ester-rich oil from Calanus finmarchicus effectively", Aquaculture, (Jul. 23, 2004).

Anthony Oxley, et al., "Fatty Acid utilisation and metabolism in caecal enterocytes of rainbow trout (*Oncorhynchus mykiss*) fed dietary fish or copepod oil", Biochemica (Oct. 5, 2005).

Olsen et al, "Atlantic Salmon, Salmo salar, utilizes wx ester-rich oil from Calanus finmarchius effectively" Aquaculture 240 (2904) 433-449 Jul. 27, 2004.

* cited by examiner

OIL COMPOSITION, FORMULATIONS COMPRISING THE OIL COMPOSITION, AND THE USE THEREOF TO REDUCE ACCUMULATION OF VISCERAL FAT, IMPROVE GLUCOSE TOLERANCE, AND PREVENT OR TREAT OBESITY RELATED DISEASES AND DISORDERS

CROSS-REFERENCE TO RELATED APPLICATIONS

This is a divisional application of U.S. application Ser. No. 13/377,572, filed 12 Dec. 2011, which is a US National Stage application of PCT/NO2010/000223, filed 11 Jun. 2010.

FIELD OF INVENTION

The present invention concerns an oil composition, particularly an oil composition that reduces accumulation of visceral fat in the body and improves glucose tolerance and hence may be used to prevent or treat obesity related diseases. Oil compositions of the present invention are comprised in pharmaceutical preparations, dietary supplements, and functional food and feed formulations.

BACKGROUND OF INVENTION

The prevalence of human obesity has increased dramatically during the last 2-3 decades in all industrialized and urbanized countries, and obesity is an emerging health threat also to people in developing countries adopting Western life-style and food habits. There are no indications that the present world-wide obesity epidemic is under control, and there are no indications of change to the better in the current trend.

Obesity has a number of consequences for human health, such as age related metabolic decline, insulin resistance, type 2 diabetes, cardiovascular disease, stroke, metabolic syndrome and early, sudden death.

The obvious cause of obesity is a net imbalance over time in the dietary energy intake and the body's energy expenditure. When people consume more energy than they expend, the excess will be stored as fat. The physiological and medical consequence of such energy imbalance is worsened by a sedentary lifestyle and by over-eating of foods rich in sugars and saturated fat.

Visceral obesity is a much higher risk factor for mortality in humans than general obesity; a strong correlation exists between obesity related diseases and visceral fat accumulation. Individuals accumulating much visceral fat and who develop a pattern of fat distribution clinically known as central obesity or abdominal obesity, are for instance particularly prone to developing diabetes (D. Callagher et al. Adipose tissue distribution is different in type 2 diabetes. *American Journal of Clinical Nutrition* 2009; 89: 807-814). A direct causal link between diabetes and visceral fat accumulation has been shown by studying the effects of surgical removal of visceral fat (Barzilai, N. and G. Gupta. Interaction between Aging and Syndrome X: New Insights on the Pathophysiology of Fat Distribution. *Annals New York Academy of Sciences* 1999; 58-72; D. M. Huffman, N. Barzilai, Role of visceral adipose tissue in aging, *Biochim. Biophys. Acta* 1790, 2009: 1117-1123). Such studies have demonstrated that visceral adipose tissue is metabolically very active and plays a predominant role in the development of obesity related health problems, and that gene expression in subcutaneous fat tissue is under control by the visceral adipose tissue. To control and reduce the health impacts of the world-wide obesity epidemic, particular attention should accordingly be paid to finding ways to counteract the development of central body obesity and accumulation of visceral fat.

There is no doubt among health professionals that healthier life-style and improved general nutrition would have the greatest positive impacts on obesity related diseases. Besides a sedentary life style, the amount of food consumed and the nature of carbohydrates and lipids used in Western foods have most often been blamed for the current obesity epidemics. But it has been difficult to predict how individual dietary components would affect the pattern of fat accumulation in the body and obesity related diseases. It has for instance been almost impossible for experts in the field to predict, based on best available knowledge in biochemistry and physiology, that consumption of fructose-sweetened, but not glucose-sweetened, beverages would promote dyslipidemia and lead to increased visceral adiposity and decreased insulin sensitivity in obese humans (K. L. Stanhope et al. Consuming fructose-sweetened, not glucose-sweetened, beverages increase visceral adiposity and lipids and decrease insulin sensitivity in overweight/obese humans. *J. Clin. Invest.* 2009; 119 (5):1322-1334). The current knowledge on what is determining the pattern of fat accumulation inside the body has first and foremost been developed as a result of experience. This applies also to the accumulating evidence for a correlation between obesity related diseases and the ratio of n-6/n-3 fatty acids in dietary lipids. When this ratio is too high, such as it is in Western diets, the impacts on human health are negative (A. P. Simpoulos. The importance of the Omega-6/Omega-3 Fatty Acid Ratio in Cardiovascular Disease and Other Chronic Diseases. *Society for Experimental Biology and Medicine* 2008; 674-688; G. Ailhaud et al. An emerging risk factor for obesity: does disequilibrium of polyunsaturated fatty acid metabolism contribute to excessive adipose tissue development? *British Journal of Nutrition* 2008; 100:461-470), in particular if a high proportion of the n-6 fatty acids in the diet consists of the "essential fatty acid" linoleic acid (C18:3n-6).

In Western diets the ratio of n-6/n-3 fatty acids ratio may be as high as 15/1, whereas this ratio most probably was around 1/1 in the diet human beings have evolved on, and which has shaped our nutrition-related genetic make-up. Nutritionists therefore recommend counteracting the negative impacts of Western diets by enriching food with plant oils, or marine oils, rich in n-3 fatty acids, thereby bringing the dietary n-6/n-3 ratio closer to what human beings have become genetically adapted to. Oils rich in n-3 fatty acids, both marine oils and plant oils, can be used to adjust the n-6/n-3 balance of dietary lipids in a more healthy direction.

In 1993, Belzung and co-authors published nutritional studies comparing the pattern of fat accumulation in Wistar rats fed high fat diets (20% w/w) having n-6/n-3 fatty acids ratios of 6.85/1 (1:1 mixture of beef tallow and olive oil), 0.3/1 (herring oil) and 0.14/1 (a concentrate of EPA (eicosapentaenoic acid=C20:5n-3) and DHA (docosahexaenoic acid=C22:6n-3) (F. Belzung et al. Fish oil n-3 fatty acids selectively limit the hypertrophy of abdominal fat depots in growing rats fed high-fat diets. *The American Physiological Society* 1993; R1111-R1118). They showed that the animals grew the same on all of these three high fat diets and that their subcutaneous and mesenteric adipose tissues were not affected. However, the animals fed herring oil or EPA/DHA concentrate in stead of beef tallow/olive oil, accumulated less abdominal adipose tissue than those fed the mixture of beef tallow and olive oil. The authors speculated that the differences they could observe were related to the highly different metabolism of these three lipid sources, including diet induced differences in the animals' membrane fatty acid composition and differences in fatty acid synthesis, prostaglandin production and modulation of hepatic enzyme activities. It should be noted that omega-3 constituted as much as 40% (used as concentrate) and 20% (herring oil) of the total dietary lipid (>20% w/w) in these studies, corresponding to a daily intake of omega-3 in the range of 0.7 to 1.4 grams. In studies with rats on the effect of EPA or DHA on expression of genes involved in lipid and glucose metabolism in white adipose tissues (T. Raclot et al. Site-specific regulation of gene expression by n-3 polyunsaturated fatty acids in rat white adipose tissues. *Journal of Lipid Research* 1997; 38:1963-1971), the daily intake of these fatty acids was 0.9 grams. In conclusion, Wistar rats consuming very high amounts of fish oil or concentrated omega-3, accumulate less visceral fat than rats feeding on a beef tallow/olive oil diet.

Despite our knowledge on the importance of life-style and nutrition on human health, the psycho-sociological obstacles are high when it comes to willingness to change bad habits. It is particularly difficult to change established food priorities in a society, even among people who understand and accept that their life-style and food habits are unhealthy. In this situation it may be desirable to have several strategies, complementary to insisting that people must change their entire way of life, which can be implemented to counteract the current obesity epidemics, in particular visceral obesity resulting in diabetes and other health problems. Pharmaceutical drugs against diabetes exist, but there are no drugs that act by primarily inhibiting the accumulation of visceral adipose tissue, known to be involved in development of diabetes 2 and other diseases. Anti-diabetic drugs in the group called thiazolidinediones works for instance by increasing the body's sensitivity to insulin, and is used in combination with diet and exercise to treat type 2 diabetes. However, these drugs lead to increased whole-body adiposity, a paradox in light of the general understanding that visceral adiposity is a conditioning factor in diabetes 2 development. Drugs in the statin group have been considered for prevention of obesity and diabetes, because drugs in this group inhibit weight gain and fat accumulation. However, they do not inhibit visceral adiposity selectively and their anti-obesity mode of action is apparently related to their ability to enhance respiratory oxygen consumption and metabolic degradation of fat.

The oil composition of the present invention is accordingly highly needed, particularly since it is without toxic side effects, as it decreases the accumulation of visceral fat even when used as a minor supplement to existing high fat Western type diets.

BRIEF DESCRIPTION OF THE DRAWINGS

FIG. 3 (A) shows the blood glucose levels during intraperitoneal glucose tolerance test in mice given the control diet (Control), high fat diet (HF) and high fat diet containing 1.5% by weight of the oil composition of the present invention (HF+1.5% CO), respectively.

FIG. 3 (B) shows the area under the curve of blood glucose levels during intraperitoneal glucose tolerance test in mice of the same groups shown in FIG. 3 (A). Data are expressed as mean±S.E. *P<0.05 for HF vs. Control; #P<0.05 for HF+1.5% CO vs. HF.

DETAILED DESCRIPTION OF THE INVENTION

The following term shall herein have the meaning as indicated below unless otherwise specifically stated:

Wax esters: Wax esters are esters of long-chain or very long-chain acids (fatty acids) and long-chain or very long-chain alcohols (fatty alcohols). Long-chain in this context means from 14 to 22 carbons, whereas very long-chain refers to 24 or more carbon atoms. Wax esters are important component in waxes. Usually, the term "wax" refers to a wide class of lipids characterized by being solids at room temperature, e.g. when it looks like honeycomb material or bees-wax. However, waxes may be both solid and liquid. They are produced by animals (beeswax, wool wax (lanolin), sperm whale wax and orange roughy oil) and plants (candelilla, carnauba, rice-bran, sugar cane (policosanol) and jojoba. All leaf surfaces and many vegetables and fruits are covered by a microcrystalline layer of wax. Waxes are used in the food, pharmaceutical and cosmetic industries for the protection of surfaces.

Wax esters of the present invention are monoesters of long-chain unsaturated fatty alcohols and long-chain unsaturated fatty acids, notably omega-3 fatty acids, and the oil composition of the present invention is completely soluble and free-flowing at room temperature.

It has been shown that the oil composition of the present invention, used as a minor supplement in a high-fat, obesity inducing Western type of diet, specifically inhibits visceral fat accumulation induced by such a diet. Moreover, it has been shown that the oil composition of the present invention can counteract impairment of heart function induced by such a diet. The oil composition of the present invention can in other words be used to counteract the most harmful effects of obesity inducing Western diets.

The oil composition of the present invention has been obtained from the marine copepod *Calanus finmarchicus*. The chemical composition of this oil differs markedly from that of other oils, and it was investigated if it would differ also regarding the possible biomedical responses it may elicit. However, there is nothing in the prior art that would lead a person skilled in the art to consider it likely that inclusion of as little as 1.5% (w/w) of the present oil composition in an obesity inducing high-fat (24% w/w) Western type of diet would result in a statistically highly significant reduction of visceral fat accumulation in rats, without affecting growth or deposition of fat in other adipose tissues. Moreover, and equally unexpected, the present oil composition reduced the visceral fat accumulation in rats fed on this high-fat diet to the same level as in rats fed on the low-fat (4% w/w) diet used as the reference diet, not inducing obesity. It is also evident that the present oil composition may counteract deterioration of healthy heart function typically seen in obesity induced type 2 diabetes, as demonstrated by high cardiac glucose metabolism even after long time feeding on an obesity inducing high-fat diet.

The n-6/n-3 proportion of fatty acids in dietary lipids affects the pattern of fat accumulation in the body. Diets in which this proportion is high (e.g. >5/1), as in high-fat Western diets, have a stronger tendency to induce central obesity and accumulation of visceral fat than diets with a lower n-6/n-3 ratio. For comparison, since the oil composition of the present invention constituted only a minor fraction of an obesity inducing high-fat Western type of diet, the n-6/n-3 fatty acid ratio was still as high as 5/1 in our experimental diet.

The oil composition of the present invention contains the n-3 fatty acids EPA (eicosapentaenoic acid=C20:5n-3) and DHA (docosahexaenoic acid=C22:6n-3), like other marine oils. However, the level of EPA and DHA is somewhat lower than in fish oil and krill oil (Table 1), whereas it is rich in stearidonic acid (SDA=C18:4n-3). Nevertheless, it might be argued that the observed inhibition of diet induced visceral obesity could be due to the presence of EPA and DHA. However, it should be borne in mind that wax esters, including marine wax esters, are digested very slowly compared to triglycerides and phospholipids and that EPA and DHA in the wax ester is not readily available for absorption as free acid. In fact, it is a common understanding among the skilled in the field that wax esters are not digestible, and that a marine wax ester rich oil like that from *Calanus finmarchicus* therefore is a poor source of EPA and DHA. Moreover, in the experiments of Belzung et al. (1993) described above, the amount of omega-3 consumed by the animals was in the range of 0.7-1.4 grams daily. By comparison, the oil composition of the present invention contributed with only 0.06 gram omega-3 daily to rats feeding on the obesity inducing high-fat diet. Accordingly, it can be concluded that the inhibition of visceral fat accumulation shown in the present invention neither can be ascribed to omega-3 as in the experiments of Belzung et al., nor can it be due to change in the ratio of n-6/n-3 fatty acids in a more healthy direction.

The oil composition according to the present invention can be derived from marine copepods, preferably a copepod of the genus *Calanus*, such as *Calanus finmarchicus*. Freshly harvested, frozen/thawed or dehydrated raw material can be used as the raw material for obtaining the oil compositions, using any method known by the skilled in the art, such as but not limited to, conventional fish oil production technology, biotechnological methods, organic solvents or supercritical fluid extraction, and cold pressing. Independent of the procedure of obtaining the oil and the yield of oil, the typical gross composition will be as shown in Table 1.

TABLE 1

Typical chemical composition of three different marine oils: (A) Copepod oil from Calanus finmarchicus caught in Norwegian waters, (B) cod liver oil from Atlantic cod *Gadus morhua*, and (C) krill oil from *Euphausia superba* caught in the Southern ocean, given in mg/g oil.

| Lipid classes and selected fatty acids | A[1] | B[2,4] | C[3,5] |
|---|---|---|---|
| Triglycerides | 10 | 955 | 260 |
| Free fatty acids | 90 | 14 | 13 |
| Saturated fatty acids | 160 | 160 | 300 |
| Monounsaturated fatty aids | 120 | 385 | 300 |
| Polyunsaturated fatty acids | 250 | 475 | 387 |
| n-3 fatty acids | 240 | 395 | 332 |
| n-6 fatty acids | 10 | 50 | 55 |
| 18:4 n-3 fatty acid (SDA) | 86 | 21 | 51 |
| 20:5 n-3 fatty acid (EPA) | 67 | 72 | 128 |
| 22:6 n-3 fatty acid (DHA) | 49 | 188 | 101 |
| Wax esters | 670 | 0 | 0 |
| Polar lipids | <50 | 18 | 670 |
| Neutral lipids | >750 | 967 | 310 |

[1]Copepod oil produced by Calanus AS (www.calanus.no).
[2]From Falch, et al., *Process Biochemistry* 2006; 41: 666-674
[3]From Phleger, et al. *Comparative Biochemistry and Physiology* Part B 2002; 131: 733-747
[4]From Standal et al., *J. Am Oil Chem Soc* 2008; 85: 105-112
[5]From Hagen et al., *Marine Biology* 2001; 139: 95-104

Besides the notable difference in gross chemical composition, the three marine oils used here for illustration purposes, are different also in their content of n-3 fatty acids (Table 1).

To illustrate the uniqueness of the oil composition according to the present invention, the corresponding compositions of conventional cod liver oil and hill oil are shown for comparison. It is evident from gross chemical analysis that these oils are highly different, in particular regarding their contents of wax esters, triglycerides, phospholipids, and of astaxanthin (not shown). It should be noted that wax esters constitute the major lipid component in the copepod oil of the present invention, unlike both cod liver oil and krill oil.

The most noteworthy difference in fatty acid composition between the three oils is the higher stearidonic acid (SDA), but lower docosahexaenoic acid (DHA) content in the copepod oil.

In the oil composition of the present invention, SDA, EPA and DHA exist to a large extent as esters with unsaturated long-chain fatty alcohols. In conclusion, the copepod oil of the present invention differs markedly from typical fish oil and krill oil in both gross chemical composition and fatty acid content. It is, however, similar to other marine oils in its overall level of n-3 fatty acids.

A typical composition of wax esters and fatty alcohols/fatty acids combinations in an oil composition of the present invention is shown in Table 2.

TABLE 2

Typical composition of wax esters and fatty alcohol/fatty acid combinations (% (w/w)) in copepod oil derived from *Calanus finmarchicus*.[1]

| Wax ester | Major fatty alcohol/fatty acid | Minor fatty alcohol/fatty acid | % (w/w) |
|---|---|---|---|
| 30:1 | 14:0/16:1 | 16:1/14:0 | 0.8 |
| 32:1 | 16:0/16:1 | 14:0/18:1 | 1.9 |
| 32:2 | 16:1/16:1 | 14:0/18:2 | 0.6 |
| 32:4 | 14:0/18:4 | 16:0/16:4 | 0.9 |
| 34:1 | 16:0/18:1 | 14:0/20:1 | — |
|  | 20:1/14:0 |  | 17.6 |
| 34:2 | 16:0/18:2 | 16:1/18:1 | 0.9 |
| 34:3 | 16:0/18:3 | 16:1/18:2 | — |
| 34:4 | 16:0/18:4 | 16:1/18:3 | 2.7 |
| 34:5 | 14:0/20:5 | 16:1/18:4 | 0.4 |
| 36:1 | 20:1/16:0 | 16:0/20:1 | — |
|  | 22:0/14:0 |  | 21.9 |
| 36:2 | 20:1/16:1 | 16:1/20:1 | 2.3 |
| 36:5 | 16:0/20:5 | 20:1/16:4 | 1.1 |
| 36:6 | 16:1/20:5 | 14:0/22:6 | 0.3 |
| 38:1 | 22:1/16:0 | 16:0/22:1 | 2.8 |
| 38:2 | 22:1/16:1 | 20:1/18:1 | 3.9 |
| 38:3 | 20:1/18:2 | 22:1/16:2 | 0.4 |

TABLE 2-continued

Typical composition of wax esters and fatty alcohol/fatty acid combinations (% (w/w)) in copepod oil derived from *Calanus finmarchicus*.[1]

| Wax ester | Major fatty alcohol/fatty acid | Minor fatty alcohol/fatty acid | % (w/w) |
|---|---|---|---|
| 38:4 | 20:1/18:3 | 22:1/16:3 | 0.9 |
| 38:5 | 20:1/18:4 | 22:1/16:4 | 5.4 |
| 38:6 | 16:0/22:6 | 16:1/22:5 | — |
| 40:2 | 20:1/20:1 | 22:1/18:1 | 5.9 |
| 40:3 | 22:1/18:2 | | 0.7 |
| 40:5 | 22:1/18:4 | 20:1/20:4 | 4.7 |
| 40:6 | 20:1/20:5 | | 1.5 |
| 42:2 | 22:1/20:1 | 20:1/22:1 | 12.7 |
| 42.6 | 22:1/20:5 | 20:1/22:5 | 1.5 |
| 42:7 | 20:1/22:6 | | 2.0 |
| 44:2 | 22:1/22:1 | | 4.9 |
| 44:7 | 22:1/22:6 | | 0.6 |

[1]Compiled from Graeve, M. and Kattner, G. Species-specific differences in intact wax esters of *Calanus hyperboreus* and *C. finmarchicus* from Fram Strait - Greenland Sea. Marine Chemistry 1992; 39: 269-281.

The marine wax esters in the oil composition of the present invention are characterized by being either mono- or polyunsaturated, with long-chain monounsaturated fatty alcohols (dominated by C16:1, C20:1 and C22:1 fatty alcohols), and a high proportion of mono- and polyunsaturated fatty acids (predominantly C16 to C22) including n-3 fatty acids SDA (C18:4), EPA (C20:5) and DHA (C22:6). The oil composition of the present invention is therefore a low-viscous and completely free-flowing liquid at room temperature.

Depending on the analytical methods used, the typical content of wax-ester of the oil composition of the present invention is 60-90%, whereas it contains 10-20% of other components such as free fatty acids, triacylglycerols, phospholipids and their residues, sterols and pigments. In certain applications, it may be advantageous or even desirable to remove free fatty acids and other components by suitable methods known to those skilled in the art. Thus, in one embodiment of the present invention the oil composition may contain up to 100% wax ester.

Figure 1:
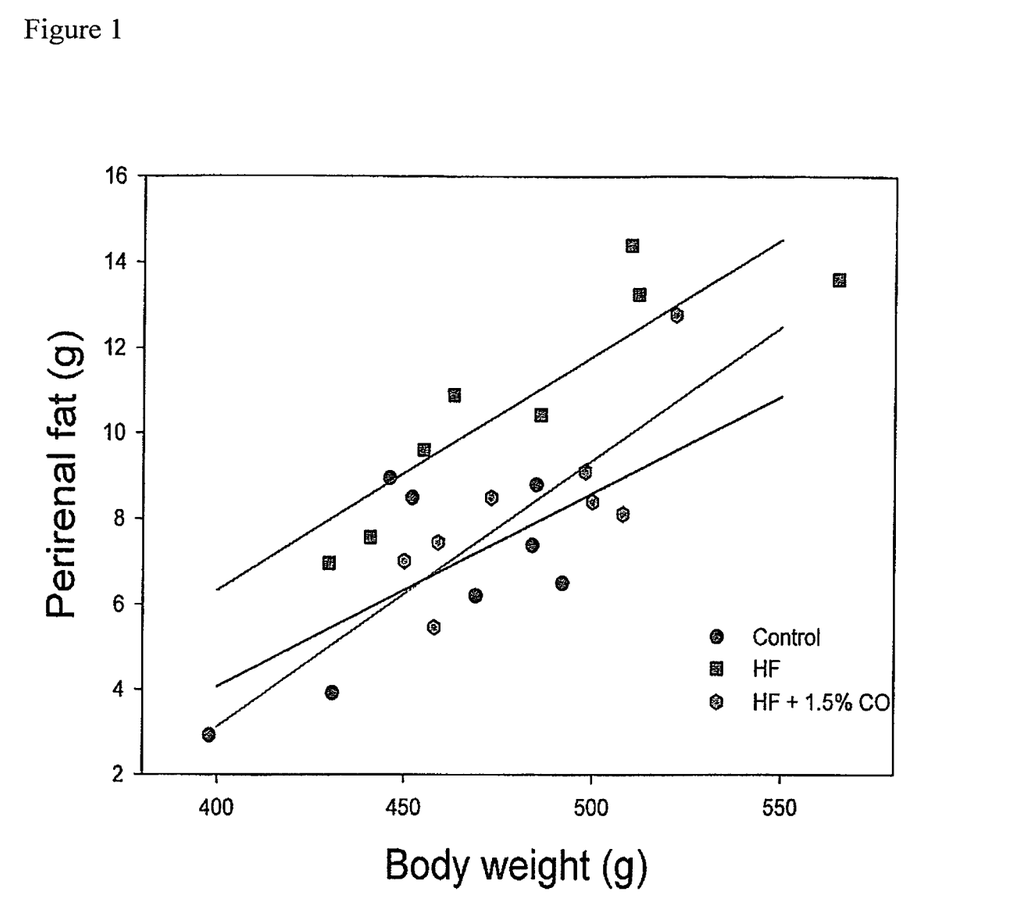
FIG. 1 shows total perirenal fat as a function of body weight in rats fed low fat reference diet (Control), obesity inducing high fat diet (HF) and obesity inducing high fat diet containing 1.5% by weight of the oil composition of the present invention, CO (Copepod Oil) (HF+1.5% CO) (n=10).
Figure 2:
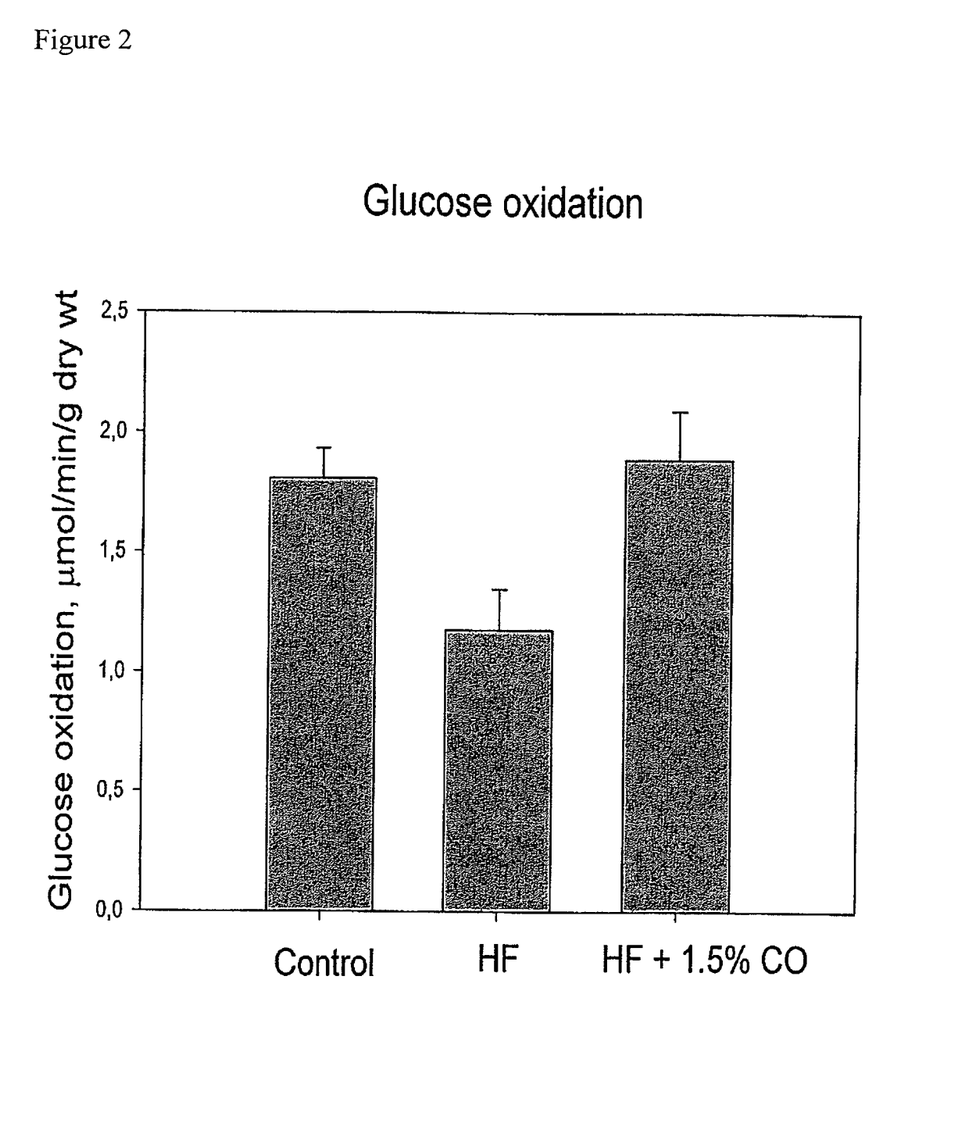
FIG. 2 shows glucose oxidation capacity (as µmol/min/g dry weight) of heart muscle tissue of rats fed low fat reference diet (Control), obesity inducing high fat diet (HF) and obesity inducing high fat diet containing 1.5% by weight of the oil composition of the present invention (HF+1.5% CO). Values are mean±95% C.I. (n=8, 6 and 6 for Control, HF and HF+1.5% CO, respectively).
Figure 3:
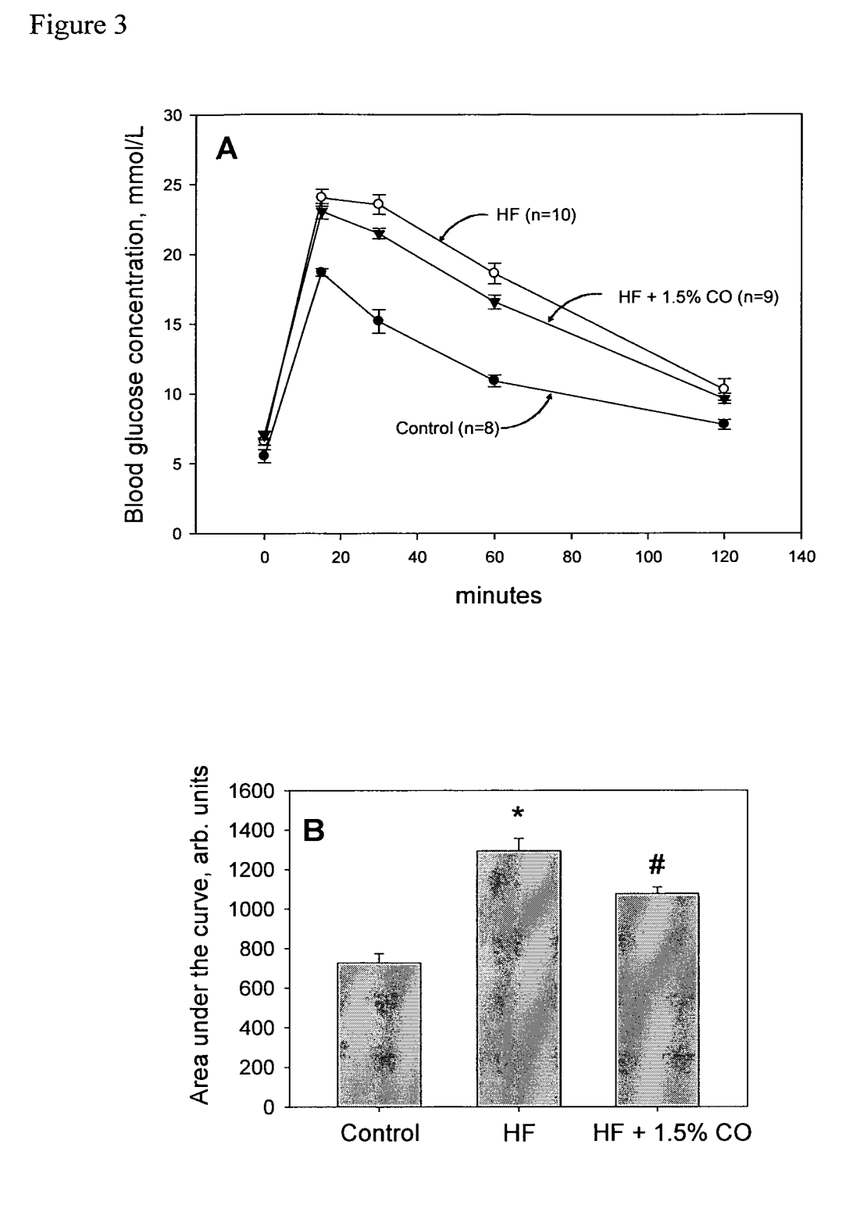

It has been shown that the oil composition of the present invention may inhibit the accumulation of visceral fat and counteract deterioration of healthy heart function induced by a high-fat Western type diet, as shown in FIGS. 1-3. Thus, the composition according to the present invention may be useful in the prevention and treatment of diseases induced by obesity, such as but not limited to type 2 diabetes.

The oil composition according to the present invention comprises from 20%, 25%, 30%, 35%, 40%, 45%, 50%, 55%, 60%, 65%, 70%, by weight up to 75%, 80%, 85%, 86%, 87%, 88%, 89% 90%, 91%, 92%, 93%, 94%, 95%, 96%, 97%, 98%, 99%, 100% by weight of wax esters. Preferably the oil composition comprises from 80%, 81%, 82%, 83%, 84%, 85%, 86%, 87% 88%, 89% by weight up to 90%, 91%, 92%, 93%, 94%, 95%, 96%, 97%, 98%, 99%, 99.5%, 100% by weight of wax esters.

Further the oil composition of the present invention comprises from 5%, 6%, 7%, 8%, 9%, 10% by weight up to 11%, 12%, 13%, 14%, 15%, 16%, 17%, 18%, 19%, 20% by weight of SDA.

The content of EPA in the oil composition may be 3%, 4%, 5%, 6%, 7%, by weight up to 8%, 9%, 10%, 11%, 12%, 13%, 14%, 15% by weight. The composition may comprise 2%, 3%, 4%, 5% by weight up to 6%, 7%, 8%, 9%, 10% by weight of DHA.

In an embodiment of the present invention an oil composition, comprising 20-100% by weight of wax esters, preferably 40-85% by weight of wax esters, wherein said wax esters consist of monoesters of predominantly mono- or polyunsaturated C16 to C22 fatty acids and predominantly monounsaturated C16, C20 and C22 fatty alcohols for use as a medicament for the prevention or treatment of abdominal obesity and obesity related disease is provided.

In one embodiment of the oil composition according to the invention 70% or more of the monounsaturated fatty alcohols of the wax esters are C16:1, C20:1 and C22:1.

In another embodiment a composition is provided wherein the obesity related disease is type 2 diabetes.

In a further embodiment the composition provided in addition comprises 5-20% by weight of stearidonic acid (SDA). An oil composition further comprising 3-20% by weight of eicosapentaenoic acid (EPA) and 2-15% by weight of docosahexaenoic acid (DHA) is provided in another embodiment of the invention.

In another embodiment of the invention the oil composition comprises fatty alcohols and SDA, DHA and EPA as monoesters.

In yet another embodiment of the present invention a composition further containing 500-4000 ppm of astaxanthin is provided.

In an embodiment of the present invention an oil composition is provided wherein the oil composition is isolated from a copepod, and in a further embodiment the copepod is of the genus *Calanus*. In yet another embodiment the copepod is of the species *Calanus finmarchicus*.

Dietary supplement formulation and functional food or feed formulation comprising an oil composition as defined according to the present invention are also provided as additional embodiments of the present invention.

In an embodiment of the invention a pharmaceutical formulation comprising an oil composition as defined according to the present invention is provided. The pharmaceutical formulation may be provided in capsules, tablets, emulsions or tonics. Further the formulation comprises one or more pharmaceutically acceptable additives selected from the group consisting of adjuvants, stabilizers, antioxidants, emulsifiers, surfactants and carriers.

In an embodiment of the present invention the use of an oil composition as defined above for the manufacture of medicaments for the prevention or treatment of abdominal obesity is provided. Further the use of the oil composition for the manufacture of medicaments for the prevention or treatment of a obesity related disease is provided, said obesity related disease is type 2 diabetes.

In yet another embodiment of the present invention a method for the prevention or treatment of abdominal obesity is provided wherein a daily amount of 0.5-5 g of an oil composition as defined above is administered to a human subject in need of such treatment. Further the method for the prevention or treatment of an obesity related disease is provided; said obesity related disease is type 2 diabetes.

In addition to its usefulness for mammals, particularly humans, it is also an embodiment of the present invention that it may used to prevent a major problem in aquacultured fish, including but not limited to salmon and trout. It is well-known among fish farmers and others who are familiar with fish farming, that fishes like salmon and trout accumulate high amounts of intestinal fat when they are feeding on compounded dry feed pellets, whereas this "quality problem" of farmed salmon is not evident in wild salmon feeding on naturally available food organisms in the ocean. Visceral fat accumulation may be so high that the intestine sometimes is merely discernible in gutted farmed fish. The reason for this quality difference between wild and farmed fishes such as salmon and trout, is not at all known by either international feed manufacturers or other people working within the aquaculture sector. It is nevertheless generally accepted that it has to do with some kind of imbalance in the artificial diet, or lack of one or more components the wild fish obtain from their natural food in the ocean. A further embodiment of the present invention is thus enrichment of fish feeds with this food source, either as a whole copepod preparation or as the oil composition of the present invention, to prevent visceral fat accumulation also in farmed fish.

The following non-limiting experimental part and examples illustrate and document the present invention.

weighed. The data are shown in Table 3 and FIG. 1. Cardiac metabolism was measured as glucose oxidation in isolated perfused hearts according to standard methodology (E. Aasum, A. M. Khalid, O. A. Gudbrandsen, O.-J. How, R. K. Berge, T. Larsen. Fenofibrate modulates cardiac and hepatic metabolism and increases ischemic tolerance in diet-induced obese mice. *Journal of Molecular and Cellular Cardiology* 2008; 44:201-209). The results are shown in FIG. 2.

In another set of experiments mice were fed for 50 days with the same diets as described for rats. For glucose tolerance test, mice were fasted for 5 h and given an intraperitoneal injection of glucose (1.3 g/kg). Blood samples were taken from the saphenous vein before injection and at 15, 30, 60, and 120 min after the injection. Blood glucose levels were determined using a glucometer (*Bayer Ascensia Contour Glucose Meter*). The results are shown in FIG. 3.

Biological Effects

TABLE 3

Biometrical data for rats fed low fat reference diet (Control), the obesity inducing high fat diet (HF) and the experimental high fat diet containing 1.5% by weight of the oil formulation of the present invention (HF + 1.5% CO). Values given for body weight at start of the feeding trials (body wt start), body weight at the end of the feeding trials (body wt sacrifice), liver weight at the end of the feeding trials (liver wt), heart weight at the end of the feeding trials (hearth wt), and the ratio between hearth weight and body weight, and tibia (shinbone) length in mm, respectively, at the end of the feeding trials. Values are mean ± 95% C.I. (n = 10).

|   | Body wt start (g) | Body wt sacrifice (g) | Liver wt (g) | Heart wt (g wet) | Heart wt (g dry) | Heart wwt/ body wt* | Heart dwt/ tibia length* |
|---|---|---|---|---|---|---|---|
| Control | 162 ± 5 | 457 ± 12 | 13.51 ± 0.75 | 1.20 ± 0.03 | 0.228 ± 7 | 2.63 ± 0.05 | 7.15 ± 0.24 |
| HF | 162 ± 3 | 483 ± 16 | 12.27 ± 0.44 | 1.21 ± 0.03 | 0.232 ± 7 | 2.54 ± 0.10 | 7.31 ± 0.19 |
| HF + 1.5% CO | 162 ± 4 | 484 ± 9 | 11.85 ± 0.37 | 1.29 ± 0.08 | 0.249 ± 14 | 2.69 ± 0.20 | 7.67 ± 0.44 |

*wwt = wet weight in gram, dwt = dry weight in gram. Values have been multiplied by 1000.

EXAMPLES

Experimental

Animal experiments were carried out at the Faculty of Medicine at the University of Tromsø, Norway. Six weeks old Wistar rats, with an average weight of 162 grams, were individually caged and housed in a room maintained at 21° C., 55% humidity and 12:12-h light-dark cycle (lights from 7 AM to 7 PM). Animals had free access to water and feed. All procedures were approved by the Norwegian Experimental Animal Board and were in accordance with the European Convention for the protection of vertebrate animals used for experimental and other scientific purposes (EST NR. 123, 1986). Rats were fed for 110 days on three different diets, which were produced by TestDiet (www.testdietcom): 1) a control diet containing 4% fat (2.37% soybean oil and 1.89% of lard, w/w), corresponding to 10% of the total dietary energy content (Control, 3.75 kcal/g); 2) an obesity-inducing high fat diet containing 24% fat (2.89% soybean oil and 20.68% of lard, w/w) corresponding to 45% of the total dietary energy content (HF, 4.65 kcal/g); 3) an experimental high fat diet containing 24% fat (2.91% of soybean oil, 19.15% lard and 1.5% of the oil formulation of the present invention), corresponding to 45% of the total dietary energy (HF+1.5% CO, 4.47 kcal/g feed). The diets were prepared without antioxidants or preservatives and stored frozen prior to feeding.

At the day of sacrifice, after administration of heparin and anesthesia, total body weight was recorded. The weight of liver and hearth were recorded after being removed from the body, and visceral (perirenal) fat was dissected out and As shown in Table 3, the average total body weight (and thus weight gain) after 110 days was the same of rats fed the two high fat (high energy) diets, whereas the rats fed on the lower energy reference diet had a lower weight gain, as expected.

Other biometrical data show that there are no notable differences between the groups. Rats in the two high fat dietary groups had the same daily feed intake and their water intake was also the same (data not shown). The reference group consumed somewhat more feed than rats in the two high fat groups, but their daily energy intake was lower, explaining their lower weight gain. In conclusion, the experiment showed that the oil composition of the present invention does not affect performance of rats fed a high fat diet and there were no signs of adverse effects on the animals.

When the animals were sacrificed after 110 days of feeding and the bellies opened up, a notable difference between the two high-fat groups could be observed with the naked eye: Rats on the experimental high-fat diet supplemented with the oil composition of the present invention, had visibly less visceral fat than the corresponding high-fat group, resembling more the visceral fat accumulation in rats that had been fed on the low fat reference diet, when comparing rats of about same size. Statistical analysis of the weights of visceral fat in the three groups confirmed this direct visual observation. Since the amount of visceral fat increases with body size, independent on feeding regime, the primary data on perirenal fat in the three dietary groups have been plotted as a function of body weight at sacrifice, as shown in FIG. 1.

Statistical treatment of these weight data revealed the following: There was a clear linear correlation between visceral fat weight and body weight in all three groups, with a level of statistical significance of p=0.034 for the reference group (Control), p=0.003 for the high-fat group (HF) and p=0.018 for the experimental group containing the oil composition of the present invention (HF+1.5% CO). Based on the fact that a statistically significant correlation exists between visceral fat weight and body weight, the statistical difference between the groups could be calculated by ANCOVA analysis, using weight as a covariate. The analysis showed that the difference between the group containing the experimental oil and the corresponding high-fat diet was statistically significant (p=0.00241), whereas there was no statistically significant difference between the experimental oil group and the low fat group. The experimental oil group and the low fat reference group, taken together, were significantly different from the high-fat group (p=0.0084). In conclusion therefore, the oil of the present invention, given as a minor supplement to high fat obesity inducing diet, inhibits the accumulation of visceral fat.

FIG. 2 shows the glucose oxidation capacity of heart muscle tissue of rats which had been feeding on the three diets. Rats on the high-fat diet (HF) had reduced glucose oxidation capacity compared to rats on the low-fat control diet (Control), whereas in rats that had been fed on the high-fat diet containing 1.5% of the present oil composition (HF+1.5% CO), glucose oxidation capacity was comparable to that of the low-fat control rats. It is evident therefore that the present oil composition may counteract deterioration of healthy heart function even after long time feeding on an obesity inducing high-fat diet.

FIG. 3(A) shows the blood glucose levels during intraperitoneal glucose tolerance test in mice given the control diet (Control), high fat diet (HF) and high fat diet with oil composition (HF+1.5% CO), respectively. FIG. 3(B) shows the area under the glucose tolerance curves shown in panel A. Data are expressed as mean±SE. *P<0.05 for HF vs Control; #P<0.05 for HF+1.5% CO vs HF.

Blood glucose levels were significantly increased during the intraperitoneal glucose tolerance test in the HF mice compared with the Control mice. These results show that feeding with a high fat diet for 50 days induced insulin resistance characteristic of type 2 diabetes. Importantly, inclusion of 1.5% of the oil composition of the present invention to the high fat diet counteracted the development of insulin resistance.

Mice on the high fat diet (HF) had reduced myocardial glucose oxidation rates compared to mice on the control diet (Control) (p<0.05). Glucose oxidation was partly restored, however, in mice that had been fed the high fat diet containing 1.5% of the present oil composition (HF+1.5% CO) (p<0.05). It is evident, therefore, that the oil composition of the present invention may counteract the reduction in myocardial glucose oxidation capacity which occur after feeding with a high fat diet.

The invention claimed is:

1. A method for reducing the risk of contracting obesity and type-2 diabetes or treatment of abdominal obesity and type 2 diabetes comprising administering to a patient in need thereof a clinically effective dosage of a composition comprising 20-100% by weight of wax esters isolated from a copepod of the genus *Calanus*, wherein said wax esters consist of monoesters of mono- or polyunsaturated C16 to C22 fatty acids and monounsaturated C16 to C22 fatty alcohols, and wherein said fatty acids are comprised of 5-20% by weight of stearidonic acid (SDA).

2. A method according to claim 1, comprising administering to a patient in need thereof a clinically effective dosage of composition comprising 40-85% by weight of wax esters.

3. A method according to claim 1, comprising administering to a patient in need thereof a clinically effective dosage of composition wherein 70% or more of the monounsaturated fatty alcohols of the wax esters are C16:1, C20:1 and C22:1.

4. A method according to claim 1, comprising administering to a patient in need thereof a clinically effective dosage of composition wherein 70% or more of the fatty alcohols of the wax esters are monounsaturated, and wherein 50% or more of the fatty acids of the wax ester are either mono- or polyunsaturated n-3 fatty acids.

5. A method according to claim 1, comprising administering to a patient in need thereof a clinically effective dosage of a composition comprises 3-20% by weight of eicosapentaenoic acid (EPA) and 2-15% by weight of docosahexaenoic acid (DHA).

6. A method according to claim 5, comprising administering to a patient in need thereof a clinically effective dosage of a composition comprises fatty alcohols and SDA, DHA and EPA as monoesters.

7. A method according to claim 1, comprising administering to a patient in need thereof a clinically effective dosage of composition containing 500-4000 ppm of astaxanthin.

8. A method according to one of claims 1 to 7, wherein the clinically effective dosage is a daily amount of 0.5 to 5 g of the oil composition.

9. A method according to claim 8, comprising administering to a patient in need thereof a clinically effective dosage of a composition isolated from the copepod species *Calanus finmarchicus*.

10. A method according to one of claim 1 to 4 or 7, comprising administering to a patient in need thereof a clinically effective dosage of a composition, wherein the composition is provided as a pharmaceutical composition in capsules, tablets, emulsions or tonics.

11. A method according to claim 10, comprising administering to a patient in need thereof a clinically effective dosage of a composition further comprising one or more pharmaceutically acceptable additives selected from the group consisting of adjuvants, stabilizers, antioxidants, emulsifiers, surfactants and carriers.

* * * * *